United States Patent [19]

Turner

[11] 4,122,113
[45] Oct. 24, 1978

[54] 9-FLUORENYL ACRYLATES

[75] Inventor: Sam R. Turner, Webster, N.Y.

[73] Assignee: Xerox Corporation, Stamford, Conn.

[21] Appl. No.: 789,173

[22] Filed: Apr. 20, 1977

Related U.S. Application Data

[62] Division of Ser. No. 596,689, Jul. 16, 1975, Pat. No. 4,046,564.

[51] Int. Cl.² .............. C07C 69/54; C07C 121/64
[52] U.S. Cl. ............................ 260/465 D; 560/221
[58] Field of Search .............. 260/465 D; 560/221

[56] References Cited

U.S. PATENT DOCUMENTS 3,883,488  5/1975  Pearson ............... 260/465 H X

OTHER PUBLICATIONS

Colter et al., J. Org. Chem. 27, pp. 1517-1520, (1962).

*Primary Examiner*—Dolph H. Torrence
*Attorney, Agent, or Firm*—James J. Ralabate; James P. O'Sullivan; Gaetano D. Maccarone

[57] ABSTRACT

Process for preparation of monomers of the formula

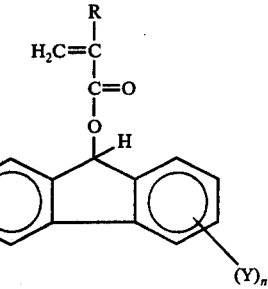

wherein R is hydrogen or methyl; X and Y are independently selected from the group consisting of $NO_2$, halogen, —CN and —$CF_3$; and $m$ and $n$ can range from 0 to 3.

Typical monomers embraced by the above formula can be prepared by Lewis Acid catalyzed esterification of methacrylic acid with a diazo derivative of an electron acceptor such as 9-diazo-2,4,7-trinitrofluorenone. These monomers can be used with other binders or polymerized by standard, free-radical techniques to polymers capable of forming self-supporting films which are useful in electrophotographic imaging members and methods.

1 Claim, No Drawings

9-FLUORENYL ACRYLATES

This is division of application Ser. No. 596,698, filed July 16, 1975 now U.S. Pat. No. 4,046,564.

BACKGROUND OF THE INVENTION

1. Field of the Invention

This invention relates to a process for preparation of monomers and the polymers derived therefrom. In addition, this invention also embraces the use of such monomers and polymers in electrophotographic imaging members and reproduction systems.

2. Description of the Prior Art

In the electrophotographic arts the photoresponsive component of the imaging member has been traditionally constructed so that one layer of photoconductive material has been primarily responsible for the absorption of imaging energies, the generation of charge carriers in response thereto and the transport of such charge carriers throughout the bulk of the layer. The electronic properties of the materials used in such a layer should be capable of rapid switching from insulating to conductive to insulating state in order to permit cyclic use of the imaging surface of said layer. The failure of a material to return to its relatively insulating state prior to the succeeding charging sequence will result in a decrease in the maximum charge acceptance of the photoconductor. This phenomenon, commonly referred to in the art as "fatigue", has in the past been avoided by the selection of photoconductive materials possessing rapid switching capacity. Typical of the materials suitable for use in such a rapidly cycling imaging system include anthracene, sulfur, selenium and mixtures thereof (U.S. Pat. No. 2,297,691), selenium being preferred because of its superior photosensitivity.

In addition to anthracene, other organic photoconductive materials, most notably poly(N-vinylcarbazole), have been the focus of increasing interest in electrophotography. Most organic photoconductive materials including poly(N-vinylcarbazole) lack the inherent photosensitivity to be competitive with selenium. This need for enhancement of the photoresponse characteristics of organic photoconductors thus lead to the formulation of these organic materials with other compounds, commonly referred to as "activators". Poly(vinylcarbazoles), for example, when sensitized with 2,4,7-trinitro-9-fluoroenone exhibit good photoresponse and discharge characteristics and (depending upon the polarity of the surface charge), low dark decay, U.S. Pat. No. 3,484,237. Ordinarily, the bulk absorption of activating electromagnetic radiation and the consequent generation of charge carriers can and often does result in some trapping of at least one species of charge carrier within the photoconductive layer and thus some impairment in the cycling characteristics of the imaging member. This disadvantage is also present where the absorption of imaging energies and the generation of charge carriers is performed by one component of a binder layer (hereinafter functionally designated as the "charge carrier generating material") and the transport of charge carriers throughout the bulk of said layer by a second chemically distinct component (hereinafter referred to as "electronically active matrix material"), U.S. Pat. No. 3,121,007 and U.K. Pat. No. 1,343,671.

In order to avoid the cycling limitations often inherent in such single layered systems, it has been proposed that the functions of (a) charge carrier generation (resulting from photoactivation) and (b) charge carrier transport can be performed more satisfactorily — (with respect to cycling) — where each of these two separate functions is performed by contiguous but separate layers (U.K. Pat. No. 1,337,228 and Can. Pat. No. 932,199). In these multi-layered configurations, absorption of imaging energies and generation of charge carriers is exclusively limited to the layer of photogenerator materials. Substantial absorption and photogeneration of charge carriers within the bulk of the charge carrier transport layer can reportedly impair the cycling characteristics of this type of composite and thus is to be avoided. In U.K. Pat. No. '228 the transport layer is capable of facile transport of either holes or electrons which are injected into it from the layer of light-absorbing charge carrier generating materials contiguous therewith. In Can. Pat. No. '199 the charge carrier transport layer is capable of facile transport of electrons injected into it from a contiguous layer of light-absorbing charge carrier generating material. Neither patent specifically discloses a polymer having an electron acceptor moiety capable of satisfactory performance in such a transport layer. The Canadian patent does indicate that such polymers can be expected to perform in a manner equivalent to binder layers containing electron acceptor materials.

Monomers having relatively weak electron acceptor groups pendant therefrom are disclosed in U.S. Pat. No. 3,418,116 and U.S. Pat. No. 3,697,264. In each instance these monomers are copolymerized with a second monomer having pendant therefrom an electron donor group. The resulting polymers reportedly are photoconductive due to the charge transfer interaction between adjacent moieties of differing electron affinities.

Attempts to prepare monomers having relatively strong electron acceptor groups have been generally unsuccessful. For example, attempts at preparation of an acrylate monomer of fluorenone by substitution of methacrylic acid for acetic acid in the process described by Colter and Wang in J. Org. Chem. 27, 1517, (1962) led to homopolymerization of the methacrylic acid.

Ordinarily, the preparation of copolymers having strong electron acceptor groups appended from their backbone is beset with a number of difficulties. Due to the strong electron affinity of such pendant groups, it is virtually impossible to initiate polymerization of such monomers by free-radical techniques, since the electron acceptor moiety quenches the free radical prior to substantial polymerization of the monomer. This problem has led to attempts at introducing electron withdrawing substituents on groups pendant from a preformed polymer which does not already inherently possess strong electron acceptor properties. This technique also encounters serious synthesis hurdles since attempts at, for example, nitration of poly(vinylfluorenone) results in degradation of the polymer and reduction in its solubility in common solvents (presumably due to crosslinking).

In both U.K. Pat. No. '228 and Can. Pat. No. '199 discussed previously, it was indicated that electron acceptor systems can be prepared by dispersing and/or dissolving a nonpolymeric electron acceptor in a suitable binder and casting or coating this composition as a film on a layer of charge carrier generating materials. In terms of long term cycling stability, such binder system transport layers are not equivalent to transport layers prepared from polymers. Such binder layers can at best be described as metastable, undergoing a progressive decline in their electronic properties. Such instability is believed to be due in part to the tendency of such non-polymeric materials to migrate within the polymeric binder and thereby cause phase separation due to crystallization. Thus, such multi-layered photoconductors would be precluded for use in the copying systems requiring repeated cycling of the imaging member over an extended period of time, since the electronic properties of the imaging member would not be capable of remaining within the machine specifications for such a device. The electron transport layer configuration of the multi-layered photoconductor is superior to the hole transport layer system in that the electron transport system is relatively insensitive to oxidative degradation and thus, unlike the hole transport analog, is capable of maintaining more stable electronic performance and thus prolonging its useful lifetime within an electrophotographic reproduction system.

Accordingly, it is the object of this invention to remedy the above as well as related deficiencies in that prior art.

More specifically, it is the object of this invention to provide a process for preparation of monomers which can be readily polymerized to polymers having the capability for facile electron transport.

It is another object of this invention to provide a multi-layered photoconductive composite wherein charge carrier generation and charge carrier transport are preformed by separate but contiguous layers.

It is yet another object of this invention to employ such multi-layered photoconductive composite in a electrophotographic reproduction method.

SUMMARY OF THE INVENTION

The above and related objects are achieved by providing a process for preparation of monomers of the formula

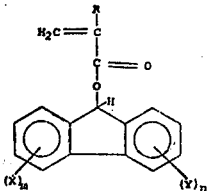

wherein
R is hydrogen or methyl;
X and Y are independently selected from the group consisting of $NO_2$, halogen, —CN and —$CF_3$; and
m and n can range from 0 to 3.

Monomers of the above formula are prepared by reacting a 9-hydrazone derivative of fluorenone or a 9-hydrazone derivative of a substituted fluorenone under oxidizing conditions to convert this starting material to the corresponding 9-diazo derivative. This 9-diazo derivative is subsequently contacted with an alpha alkyl substituted acrylic acid and the esterification of these two ingredients catalyzed by the introduction of a Lewis acid. The monomers prepared as described above can be used in combination with other binders or polymerized by standard free-radical techniques to polymers capable of forming self-supporting films useful in the electrophotographic imaging members and methods.

DESCRIPTION OF THE INVENTION INCLUDING PREFERRED EMBODIMENTS

Preliminary to preparation of the monomers of this invention, a 9-diazo fluorene or a 9-diazo substituted fluorene is prepared by the technique disclosed by Wang and Colter in J. Org. Chem. 27, 1517 (1962). According to their process, fluorenone or a nitro substituted fluorenone is reacted with hydrazine under the appropriate conditions thereby yielding the corresponding 9-hydrazone derivative. The following series of equations are representative of a typical embodiment of the process of this invention:

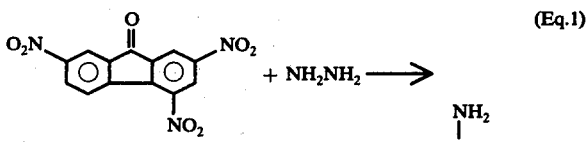

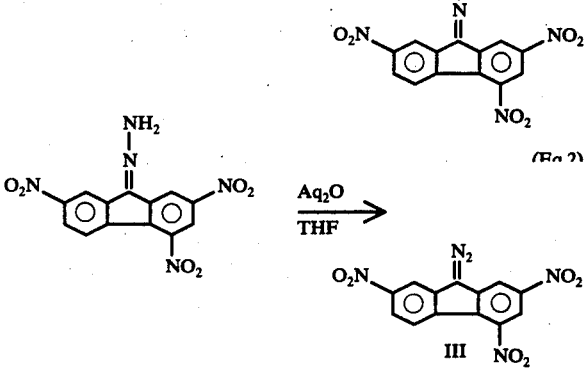

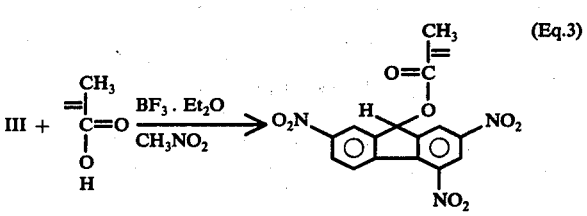

In equation 1, an appropriate amount of 2,4,7-trinitrofluorenone is reacted with hydrazine in the manner described in the previously referenced Wang and Colter publication to yield the 9-hydrazone derivative of this material.

In equation 2, the 9-hydrazone derivative is thereafter oxidized to the corresponding 9-diazo derivative. This is achieved by simply dissolving the 9-hydrazone derivative and an oxidizing agent in a suitable solvent (e.g. tetrahydrofuran, chloroform, acetone etc.), and heating to boiling under reflux conditions.

The relative concentration of the 9-hydrazone derivative to the oxidizing agent should be sufficient to effectively convert all of the 9-hydrazone compounds to their corresponding 9-diazo derivatives. In a preferred embodiment of the process of this invention, the reaction medium contains an excess of oxidizing agent relative to the concentration of the hydrazone compound. The temperature within the reaction vessel prevailing during such oxidation reaction is only limited by the boiling point of the solvent contained therein. In the event it is desirable to operate at temperatures in excess of the boiling point of such solvents, the reaction vessel need only be pressurized.

The volume of solvent present in the reaction vessel should be sufficient to effectively dissolve both of the major reactants and thereby permit a homogeneous type oxidation of the 9-hydrazone to the corresponding 9-diazo derivative. The reaction time necessary to effect a satisfactory oxidation of the 9-hydrazone is yield related; the longer the oxidation reaction is allowed to proceed, the more of the desired product that is produced. After the reaction has proceeded for the prescribed interval, the contents of the reaction vessel are cooled, the solids contained therein removed by filtration (and discarded), and the liquid contents of the flask evaporated. The materials remaining in the reaction vessel can thereafter be collected and purified for removal of residual traces of oxidizing agent by recrystallization from nitromethane.

Typical of the oxidizing agents which are suitable for use in this step of the process include argentous oxide, peroxides, permanganates, and certain nitrates.

In equation 3, the product of the preceeding reaction is combined with methacrylic acid in trinitromethane and a Lewis acid subsequently added to effect catalysis of the esterification reaction between the 9-diazo derivative of nitrofluorenone with the methacrylic acid. The relative molar concentration of 9-diazo nitrated fluorenone to methacrylic acid in the trinitromethane can range from about 1:5 to 1:10 with 1:7 being preferred. The reaction conditions prevailing during such esterification are not believed to be critical to the occurrence of this condensation reaction, however, in order to obtain satisfactory yields it is preferable that such reaction take place in a nonoxidizing atmosphere and that the temperature prevailing during such reaction range from about 20° to about 60° C. The Lewis acid suitable for use in initiating the esterification of the methacrylic acid with the 9-diazo derivative of nitrated fluorenone can include any of the Lewis acids presently disclosed in the technical literature. The preferred Lewis acids useful in this process include boron trifluoride-etherate, aluminum chloride, and stannous chloride.

The volume of solvent in which this esterification reaction is carried out is not believed to be of critical importance. Sufficient solvent should be used to adequately dissolve the reactants contained therein and yet not exceed that amount which would require extended reaction time for completion of the esterification reaction. The monomer which forms during this step of the process can be separated from the trinitromethane solution by rotary evaporation at temperatures in the range of from about 40°–60° C. The residue remaining is dissolved in benzene, for precipitation of residual traces of diazo compounds, and the benzene solution evaporated to an oily residue which ultimately crystallizes. The monomer thus obtained is further purified by washing with ether.

Monomers prepared by the above process can be readily polymerized by standard free radical techniques. In a preferred embodiment of this invention, the monomer obtained by the representative synthesis described above is dissolved in acetone containing 1 weight percent azobisisobutyronitrile (AIBN) and, thereafter, taken through two freeze-thaw cycles thereby insuring that the solvent vehicle is free from oxygen. The polymerization is conducted in a non-oxidizing atmosphere at temperatures in the range of from about 40° C. to about 80° C. The polymeric product thus obtained can be solvent coated from any one of a number of common solvents. Apparently, the polymeric products prepared according to this process are capable of forming charge transfer complexes with dimethylformamide and dimethylsulfoxide and thus these solvents are to be avoided in the casting of the polymer where clear films are required.

In addition to formation of homopolymers from these monomers, these monomers can also be copolymerized with other addition monomers. Such other addition monomers can contain pendant groups capable of charge transfer interaction with the pendant fluorenyl and substituted fluorenyl groups of these monomers. Polymeric compositions prepared from these monomers can also serve as binders or solid solution matrices for other photoconductive materials.

The monomers, homopolymers and copolymers described hereinabove can be used alone or in combination with one another, or in combination with other monomers and/or polymers in electrophotographic imaging members and methods. For example, the electronically active monomers of this invention can be dissolved/dispersed in a polymeric binder and films prepared therefrom. The polymeric binder can itself be electronically active or electronically inert. In the case where these monomers are used in conjunction with an active binder, such as poly(N-vinylcarbazole), charge transfer interaction will occur thereby forming a photoconductive composition having substantial spectral response in the visible region of the electromagnetic spectrum. These electronically active monomers are appreciably more stable in both electronically active and electronically inert binders than, for example, 2,4,7-trinitro-9-fluorenone and, thus, higher loadings of such monomers can be used in conjunction with such binders without occasioning phase separation of the materials of such compositions.

Polymers and copolymers prepared from the above monomers can be formed into tough, flexible, chemically stable films by conventional means with conventional equipment. The homopolymers prepared from the above monomers are only slightly photosensitive in the visible region of the electromagnetic spectrum and, therefore, are high suitable for use as charge carrier transport layers in composite photoconductive insulating layers of the type disclosed in Canadian Pat. No. 932,199. This composite photoconductor consists essentially of a layer of photoconductive material capable of substantial spectral response in the visible region of the electromagnetic spectrum and contiguous therewith an insulating layer of charge transport material incapable of substantial spectral response in the visible region of the electromagnetic spectrum. Upon photoactivation of this composite, charge carriers are generated in the photoconductive layer and injected into the charge carrier transport layer. The materials selected for these respective layers must be sufficiently closely matched electronically so as to permit the injection of carriers from one layer into the other. Where the polymeric materials prepared from the monomers of this invention are used in the transport layer, the resulting transport layer will be capable of facile transport of electrons. Photoconductive pigments which can be used in combination with transport layers prepared from the polymers derived from the monomers of this invention include inorganic crystalline photoconductors such as cadmium sulfide, cadmium sulfoselenide, cadmium selenide, zinc sulfide, zinc oxide, trigonal selenium, and mixtures thereof. Typical inorganic photoconductive glasses which can be used in this photogenerator layer are amorphous selenium and its alloys (especially alloys of arsenic and tellurium). Representative of the organic photoconductors which can be used in such a photogenerator layer include phthalocyanine pigments and the photoinjecting pigments of benzimidazole, perylene, quinacridone, indigoid and polynuclear quinones.

In a typical composite photoconductive layer of the type referred to hereinabove, the photoconductive layer can range in thickness from about 0.02 to about 20 microns and the charge carrier transport layer a thickness in the range of from about 5 to about 100 microns; the ratio of thickness of the photoconductive layer to the transport layer being in the range of from about 1:2 to about 1:200.

The polymers prepared from the monomers of this invention are also suitable as electronically active binders for photoconductive pigments. In addition, the polymers of this invention can be sensitized by combining them with dyestuffs and/or electron donors (relative to the electron withdrawing substituent of the polymer). These electron donors can be monomeric or polymeric. Upon combination of the polymers of this invention with Lewis bases, charge transfer interaction will occur thereby forming a highly colored charge transfer complex which is photoresponsive to light throughout a substantial portion of the visible band of the electromagnetic spectrum. This photoconductive composition can be used alone or in combination with other materials in electrophotographic imaging members and methods.

Where these monomers are copolymerized with other monomers, the electronic properties of the copolymer will differ from the properties of the homopolymer. In the event that these monomers are copolymerized with monomer devoid of carbocylic or heterocyclic constituents, the resultant copolymer will generally be less electronically active and less intensely colored than the homopolymer prepared from this same monomer. Where the comonomer does contain a carboxylic and/or heterocyclic constituent, the electronically active constituent of the monomers of this invention may undergo some charge transfer interaction with the carbocyclic and/or heterocyclic constituent on the adjacent structural unit of the copolymer backbone or with the carbocyclic and/or heterocyclic constituent on adjacent copolymer backbones. The presence of such carbocylic and/or heterocyclic constituents can also be expected to increase the mobility of holes generated upon photoexcitation of the copolymer and/or holes which are injected into the copolymer from another source of charge carrier. These "intrachain" charge transfer copolymers will thus exhibit bipolarity and can be used as a matrix for other photoconductive pigments and dyes without appreciable trapping of either species of charge carrier by the matrix. Of course, the bipolar character of such a system presumes that the photoconductive pigments and dyes do not trap either species of charge carrier.

The Examples which follow further define, describe and illustrate the preparation and use of the monomers and polymers of this invention. Apparatus and techniques used in preparation and evaluation of these materials are standard or as hereinbefore described. Parts and percentages appearing in such examples are by weight unless otherwise stipulated.

EXAMPLE I

Synthesis and polymerization of 2,4,7-trinitro-9-fluoroenyl methacrylate;

2,4,7-trinitro-9-fluorenone is contacted with stoichiometric quantities of hydrazine in an appropriate solvent, heated to a temperature in a range of from about 80 to about 85° C. and the materials allowed to react for a period of at least 2 hours. At the end of this interval, the desired product forms a precipitate which can be separated from the unreacted materials and solvent vehicle by simple filtration techniques. The product which is recovered can be subsequently purified by washing in an appropriate solvent. Chemical analysis of the product confirms it to be the hydrazone derivative of 2,4,7-trinitro-9-fluorenone. Following air drying, this hydrazone derivative is placed in a reaction vessel with a stoichiometric excess of argentous oxide, and sufficient tetrahydrofuran added to dissolve these materials. The solution is then heated to boiling under reflux conditions for a period of about 5 hours. The precipitate which forms during this reaction is separated from the solution by filtration and discarded. The liquid of the solution is then evaporated sufficiently until crystallization of diazo product occurs. Such crystals are separated from the liquid by filtration and purified by recrystallization from nitromethane. Chemical analysis of the purified product indicates it to be the 9-diazo derivative of 2,4,7-trinitro-9-fluorenone.

About 10 parts of this 9-diazo derivative is suspended in 150 milliliters of tetrahydrofuran and methacrylic acid added, the quantity of metacrylic acid being 7 fold the stoichiometric amounts required for esterification with the diazo compound. Subsequent to addition of the methacrylic acid to the reaction medium, boron trifluoride etherate is added to the contents of the reaction vessel. The gram equivalent molecular weight of the boron trifluoride etherate is equivalent to the gram equivalent molecular weight of the diazo compound. The contents of the reaction vessel are allowed to react at room temperature for a period of about 1 hour. The liquid phase of the reaction mass is removed by rotary evaporation at 50° C. The yellowish solid which is recovered is subsequently washed in 150 milliliters of water with vigorous agitation for a period of 2 hours. The solids are then removed from the aqueous solution by filtration, dried, and dissolved in 50 milliliters benzene. The solution is heated to boiling under reflux conditions, the particulates which precipitate are removed by filtration and discarded and the remaining liquid evaporated to an oily residue which eventually crystallizes. These crystals are purified by washing with ether. Chemical analysis indicates the crystalline product to be 2,4,7-trinitro-9-fluorenylmethacrylate, which exhibited a melting point of 148°–150° C.

About 10 parts of this monomer is thereafter dissolved in a tetrahydrofuran solution containing 0.1 part azobisisobutyronitrile. The polymerization is carried out in a nonoxidizing atmosphere utilizing conventional techniques and equipment. After a 24 hour period, the contents of the flask are emptied into a 1000 milliliters of methanol whereupon the polymer solids form a precipitate. The polymer is separated from the liquid by filtration and thereafter dried. The intrinsic viscosity of the polymer in $[\eta]_{30° C.}^{THF} = 0.128$.

About 10 parts of this polymer is dissolved in 25 milliliters of tetrahydrofuran and the resulting solution draw bar coated on a ball grained aluminum plate. The dry film thickness of the coating is approximately 15 microns. Electrophotographic evaluation of this imaging member indicates that it possesses good photoresponse between 3500 and 4200 angstrom units. This imaging member is thereafter placed in a vacuum evaporator and a thin film of amorphous selenium deposited on the free surface of the polymeric coating. The thickness of this selenium deposit is approximately 2 microns. The resulting photoconductive composite is thereafter evaluated electrophotographically by charging the surface of the selenium layer to a negative potential of about 600 volts followed by exposure to a light and shadow image. The illumination source of the image formation is a tungsten lamp. The latent image produced on the surface of the imaging member is thereafter developed with positively charged toner particles and the toner image transferred to a sheet of paper. The surface of the selenium layer is wiped clean of toner residues and the reproduction cycle repeated. Copy quality is acceptable and such acceptable copy quality is reproducible.

EXAMPLE II

About 40 parts by weight of the monomer prepared according to the procedures of Example I and 60 parts polyethylene terephthalate (Mylar 49000, E. I. du Pont de Nemours and Company) are dissolved in a common solvent and the resulting solution draw bar coated on a ball-grained aluminum plate. The dry film thickness of the resulting coating is approximately 25 microns. Upon substantially complete evaporation of solvent residues from this coating, the coated plate is placed in a vacuum evaporator and an amorphous selenium film vacuum deposited on the free surface of this coating. The thickness of this selenium layer is approximately 1 micron. This composite photoconductive imaging member is evaluated in the same manner described in Example I. The electrophotographic response of the imaging member is somewhat slower, however, copy quality if acceptable and such quality is reproducible.

EXAMPLE III

The monomer of Example I is dissolved along with poly(N-vinylcarbazole) in a common solvent and the resultant solution draw bar coated on a ball grained aluminum plate. The molar concentration of monomer in this composition is equivalent to the molar concentration of carbazole units of the polymer. The resulting composition is highly colored due to charge transfer interaction between the monomer and the photoconductive polymer. In addition, the composition is free of crystallization indicating improved solubility of the monomer in this polymer over that of an equivalent amount of 2,4,7-trinitro-9-fluorenone. Aging studies conducted on the composition prepared from the monomer of this invention and polyvinylcarbazole indicated that the lack of crystallization in the initially formed composition is preserved throughout the useful life of the photoconductor.

EXAMPLE IV

About 4 parts of the monomer prepared by Example I is copolymerized with 1 part methylmethacrylate in the same manner described in Example I. The copolymer thus produced is draw bar coated over a thin film of amorphous selenium, which has previously been vacuum evaporated on a ball-grained aluminum plate. The amorphous selenium layer is approximately 1 micron in thickness and the layer of copolymer approximately 15 microns in film thickness. The polymeric film prepared from the copolymer of this example is significantly lighter in color than homopolymers prepared from this same monomer and this is more suitable for use in composite photoconductive layers where the image information is to be transmitted through this layer to the photoconductive layer. Electrophotographic evaluation of this member proceeds in a manner described in Example I except that the surface of the polymeric layer is sensitized by charging to a positive potential and the latent image which is formed is developed with negatively charged toner particles. The electrophotographic response of the imaging member is acceptable and copy quality is acceptable and reproducible.

What is claimed is:
1. Monomers of the formula

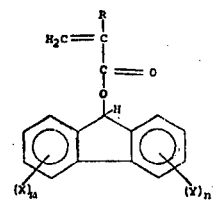

where
R is hydrogen or methyl;
X and Y are independently selected from the group consisting of $NO_2$, halogen, —CN and —$CF_3$; and
$m$ and $n$ can range from 0 to 3.

* * * * *